US010723633B2

(12) United States Patent
Gemoets et al.

(10) Patent No.: US 10,723,633 B2
(45) Date of Patent: Jul. 28, 2020

(54) PROCESS FOR RECOVERING HEAVY METAL IONS

(71) Applicant: BP Corporation North America Inc., Naperville, IL (US)

(72) Inventors: Dominique Gemoets, Belgium (BE); Wim Verbeeck, Belgium (BE)

(73) Assignee: BP Corporation North America Inc., Houston, TX (US)

( * ) Notice: Subject to any disclaimer, the term of this patent is extended or adjusted under 35 U.S.C. 154(b) by 296 days.

(21) Appl. No.: 15/392,038

(22) Filed: Dec. 28, 2016

(65) Prior Publication Data
US 2017/0190594 A1   Jul. 6, 2017

Related U.S. Application Data

(60) Provisional application No. 62/273,588, filed on Dec. 31, 2015.

(51) Int. Cl.
C01G 51/06      (2006.01)
C07C 51/41      (2006.01)
(Continued)

(52) U.S. Cl.
CPC ............ *C01G 51/06* (2013.01); *C02F 1/5236* (2013.01); *C07C 51/00* (2013.01); *C07C 51/41* (2013.01);
(Continued)

(58) Field of Classification Search
None
See application file for complete search history.

(56) References Cited

U.S. PATENT DOCUMENTS 3,959,449 A * 5/1976 Shigeyasu ............... B01J 37/22
                                                       423/488
5,723,656 A   3/1998 Abrams
5,955,394 A * 9/1999 Kelly ........................ B01J 31/04
                                                       423/139

FOREIGN PATENT DOCUMENTS

BE         792520 A   *  6/1973    ........... B01J 23/8892
CN    103627904 A      3/2014
(Continued)

OTHER PUBLICATIONS

Zhang, P. et al. Hydrometallurgical Process for Recovery of Metal Values from Spent Lithium-ion Secondary Batteries, vol. 47, No. 2-3, Hydrometallurgy, Jan. 1, 1998, p. 259-271.

*Primary Examiner* — Melissa S Swain
(74) *Attorney, Agent, or Firm* — McDonnell Boehnen Hulbert & Berghoff LLP

(57) ABSTRACT

A process is provided for recovering a heavy metal from a waste stream resulting from a process for producing aromatic carboxylic acid by liquid-phase oxidation of an aromatic feedstock compound in the presence of a heavy metal catalyst. The process comprises: (a) producing a carbonate salt precipitate of the heavy metal by adding a source of metal ions and carbonate or bicarbonate ions into the waste stream; (b) separating the precipitate from the waste stream; (c) washing the precipitate with an alkali solution having metal ions therein, wherein at least a portion of the metal ions in the alkali solution are the same as at least a portion of metal ions in the source of metal ions and carbonate or bicarbonate ions; and, (d) recovering the washed precipitate wherein the washed precipitate comprises the heavy metal ions. In one embodiment, the aromatic carboxylic acid comprises terephthalic acid.

21 Claims, 1 Drawing Sheet

(51) Int. Cl.
  *C02F 1/52* (2006.01)
  *C22B 3/12* (2006.01)
  *C22B 3/22* (2006.01)
  *C07C 51/00* (2006.01)
  *C07C 51/487* (2006.01)
  *C02F 101/20* (2006.01)
  *C02F 103/36* (2006.01)

(52) U.S. Cl.
  CPC .............. *C07C 51/487* (2013.01); *C22B 3/12* (2013.01); *C22B 3/22* (2013.01); *C02F 2101/20* (2013.01); *C02F 2103/36* (2013.01)

(56) References Cited

FOREIGN PATENT DOCUMENTS

| CN | 103861650 A |   | 6/2014  |             |
|----|-------------|---|---------|-------------|
| GB |    899288 A | * | 6/1962  | .............. B01J 41/07 |
| JP |  07196323 A | * | 8/1995  |             |
| JP |  08283204 A | * | 10/1996 |             |
| JP | H09 157214  |   | 6/1997  |             |
| JP | H09-157214 A |  | 6/1997  |             |

* cited by examiner

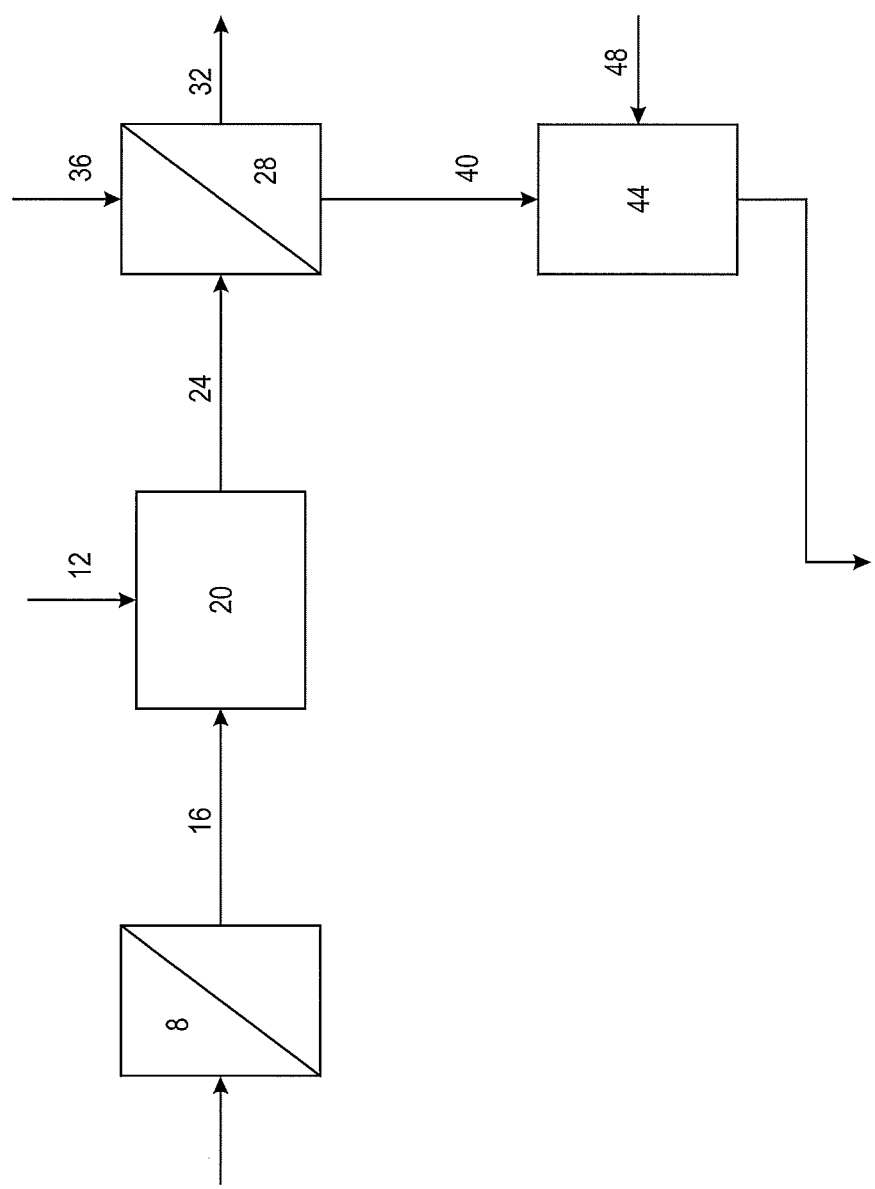

PROCESS FOR RECOVERING HEAVY METAL IONS

CROSS-REFERENCE TO RELATED APPLICATION

This Application claims the benefit of U.S. Provisional Application No. 62/273,588, filed on Dec. 31, 2015, which is hereby incorporated herein by reference in its entirety for all purposes.

FIELD OF THE INVENTION

This invention relates generally to the field of heavy metal recovery.

BACKGROUND OF THE INVENTION

Heavy metals are useful as catalysts in many industrial processes. In many of these processes, a portion of the heavy metals may enter into waste streams, such was wastewater streams. Recovery of the heavy metals from these waste streams is often desirable so that the heavy metal may be reused as a catalyst. In other applications, it may be desirable to remove the heavy metals from waste streams before the waste streams are released to the environment.

In one particular known industrial process, aromatic carboxylic acids are made by liquid-phase oxidation of aromatic feedstock in an aqueous acetic acid solvent in the presence of air and a heavy metal catalyst. The heavy metal catalyst may be, for example, a bromine promoted catalyst that comprises cobalt and manganese. The oxidation yields aromatic carboxylic acid together with by-products, including partial and intermediate oxidation products of the aromatic feedstock, and acetic acid reaction product. Water is also generated as a by-product in the reaction.

The aromatic carboxylic acid produced in the oxidation process is withdrawn from the reactor as a slurry of crystals in a mother liquor comprising mainly aromatic carboxylic acid together with water, organics and dissolved catalyst components (cobalt and manganese in the form of their acetates). In typical known processes, after separation of the aromatic carboxylic acid product from the mother liquor of the slurry, a major part of the mother liquor and its catalyst heavy metal content are recycled to the oxidation reactor, and the minor part is purged from the system to avoid undue build-up of organic contaminants within the reaction system. The mother liquor purge is treated to recover acetic acid for recycle to the oxidation reaction, precipitate the catalyst metals as carbonates or bicarbonates so that they can then be recovered for further treatment, if necessary, and recycled to the oxidation reactor.

Consequently, there is always a need to recover heavy metals more efficiently for reuse in a range of industrial processes.

BRIEF SUMMARY

According to one aspect of the invention, a process is provided for recovering a heavy metal from a waste stream resulting from a process for producing aromatic carboxylic acid by liquid-phase oxidation of an aromatic feedstock compound in the presence of a heavy metal catalyst. The process comprises: (a) producing a carbonate salt precipitate of the heavy metal by adding a source of metal ions and carbonate or bicarbonate ions into the waste stream; (b) separating the precipitate from the waste stream; (c) washing the precipitate with an alkali solution having metal ions therein, wherein at least a portion of the metal ions in the alkali solution are the same as at least a portion of metal ions in the source of metal ions and carbonate or bicarbonate ions; and, (d) recovering the washed precipitate wherein the washed precipitate comprises the heavy metal ions.

According to another aspect of the invention, a process is provided for recovering cobalt from a liquid medium containing a basic cobalt salt. The process comprises: (a) producing a cobalt carbonate precipitate by adding a source of metal ions and carbonate or bicarbonate ions into the liquid medium; (b) separating the cobalt carbonate precipitate from the liquid medium; (c) washing the cobalt carbonate precipitate with an alkali solution having metal ions therein, wherein the metal ions in the alkali solution are the same as the metal ions in the source of metal ions and carbonate or bicarbonate ions, the washing being performed without resuspending the precipitate; and, (d) recovering cobalt from the washed precipitate in the form of cobalt carbonate.

Those skilled in the art will recognize other aspects of the invention in view of the description that follows.

BRIEF DESCRIPTION OF THE DRAWINGS

For a detailed description of the preferred embodiments of the invention, reference will now be made to the accompanying drawings in which:

FIG. 1 illustrates, in schematic form, an embodiment of operating the process of this invention.

DETAILED DESCRIPTION OF THE PREFERRED EMBODIMENTS

In a process according to one embodiment of the present invention, one or more heavy metals are recovered from a waste stream resulting from an aromatic carboxylic acid production process via liquid-phase oxidation of aromatic feedstock compounds in the presence of a heavy metal catalyst. The process comprises: (a) producing a carbonate salt precipitate of the heavy metal by adding a source of metal ions and carbonate or bicarbonate ions into the waste stream; (b) separating the precipitate from the waste stream; (c) washing the precipitate with an alkali solution having metal ions therein, wherein at least a portion of the metal ions in the alkali solution are the same as at least a portion of metal ions in the source of metal ions and carbonate or bicarbonate ions; and, (d) recovering the washed precipitate which comprises the heavy metal ions.

The aromatic feedstock compound can be any aromatic compound that has oxidizable substituents which can be oxidized to a carboxylic acid group. For example, the oxidizable substituent can be an alkyl group such as a methyl, ethyl, or isopropyl group. It can also be a partially oxidized alkyl group such as an alcohol group, aldehyde group or ketone group. The aromatic portion of the aromatic feedstock compound can be a benzene nucleus or it can be bi- or polycyclic, for example, a naphthalene nucleus. The number of oxidizable substituents on the aromatic portion of the aromatic feedstock compound can be equal to the number of sites available on the aromatic portion of the aromatic feedstock compound, but is generally fewer, preferably 1 to 4, and even more preferably 2 or 3.

Examples of suitable aromatic feedstock compounds include toluene, ethylbenzene, o-xylene, meta-xylene, para-xylene, 1-formyl-4-methylbenzene, 1-hydroxymethyl-4-methylbenzene, 1,2,4-trimethylbenzene, 1-formyl-2,4- methylbenzene, 1,2,4,5-tetramethylbenzene, alkyl, hydroxymethyl, formyl, and acyl substituted naphthalene compounds such as 2,6- and 2,7-dimethylnaphthalene, 2-acyl-6-methylnaphthalene, 2-formyl-6-methylnaphthalene, 2-methyl-6-ethylnaphthalene, 2,6-diethylnaphthalene, and the like.

For example, when oxidized, para-xylene produces terephthalic acid, meta-xylene produces isophthalic acid, and 2,6-dimethylnaphthalene produces.

Methods for oxidizing aromatic feedstock to the corresponding aromatic carboxylic acid using a liquid phase, heavy metal catalyzed oxidation reaction are known in the art. For example, such processes are disclosed in U.S. Pat. No. 5,723,656. In general, suitable heavy metal oxidation catalysts include those metals having an atomic number of about 21 to about 82, inclusive. In some embodiments, the oxidation catalysts include a mixture of cobalt and manganese. In some embodiments, the oxidation solvent is a low molecular weight aliphatic monocarboxylic acid having 2 to about 6 carbon atoms, inclusive, mixtures thereof with water. In some embodiments, the solvent is acetic acid or mixtures of acetic acid and water. A reaction temperature of about 145° C. to 235° C. is typical, and the reaction pressure is such that the reaction mixture is under liquid phase conditions. A promoter such as a low molecular weight ketone having 2 to about 6 carbon atoms or a low molecular weight aldehyde having 1 to about 6 carbon atoms can be also used. Bromine promoter compound known in the art such as hydrogen bromide, molecular bromine, sodium bromide and the like can also be used. A source of molecular oxygen is also required, and typically it is air. For the conversion of para-xylene to terephthalic acid the source of molecular oxygen can vary in molecular oxygen content from that of 10% molecular oxygen to oxygen gas.

The catalyst employed in the oxidation step for producing aromatic carboxylic acid comprises cobalt, manganese, and bromine components, and can additionally comprises accelerators, or promoters, known in the art.

In one embodiment of the present invention, the waste stream resulting from the liquid phase oxidation typically comprises residual amounts of aromatic acids, catalysts, solvents, and water. In one embodiment in which terephthalic acid is produced, the the aster stream includes terephthalic acid, cobalt/manganese acetate, bromides, terephthalates and benzoates, residual amounts of acetic acid, and water. In another embodiment, the waste stream comprises cobalt acetate and manganese acetate.

Examples of suitable source of carbonate or bicarbonate ions include sodium carbonate, sodium bicarbonate, a mixture of sodium carbonate and sodium bicarbonate, potassium carbonate, potassium bicarbonate, and a mixture of potassium carbonate and potassium bicarbonate. When the source of metal ions and carbonate or bicarbonate ions is sodium carbonate, sodium bicarbonate, or a mixture thereof, the alkali solution used to wash the heavy metal carbonate salt precipitate can be sodium hydroxide. Typically, the concentration of sodium hydroxide solution used is at least 0.5%. Preferably, the concentration is at least 1%. More preferably, sodium hydroxide solution of at least 5% is used.

According to one embodiment of the process, the source of metal ions and carbonate or bicarbonate ions used in the process is sodium carbonate, sodium bicarbonate or a mixture thereof. The source of metal ions and carbonate or bicarbonate ions is added until pH is 7 to 9.5 to produce the carbonate salt precipitate of the heavy metal.

In one embodiment, the heavy metal recovery process further comprises washing the precipitate, which has been washed with the alkali solution, with water before recovering the carbonate salt precipitate of the heavy metal.

In one embodiment wherein sodium carbonate, sodium bicarbonate or a mixture thereof is used as the source of metal ions and carbonate or bicarbonate ions, the alkali solution in step (c) is sodium hydroxide solution. In yet another embodiment, the process further comprises, after washing the precipitate with sodium hydroxide solution, quantitating the sodium ions in the precipitate recovered in step (d). In one embodiment wherein the sodium ions in the precipitate is quantitated, the cobalt/sodium ratio in the catalyst is at least 10.

According to one embodiment of the process, washing the carbonate salt precipitate of the heavy metal is performed without resuspending the precipitate.

In one embodiment, the process further comprises converting the carbonate salt of the heavy metal into catalyst suitable for the liquid-phase oxidation for producing the aromatic carboxylic acid.

According to one aspect of the present invention, the waste stream from which the heavy metal is recovered is a slurry which comprises organic acidic by-products generated in the oxidation reaction, the heavy metal and promoter catalyst components, residual amount of the low molecular weight aliphatic monocarboxylic acid used as the oxidation solvent for the liquid-phase oxidation reaction, and water. For example, in a terephthalic acid process wherein cobalt acetate and/or manganese acetate are used as catalyst with bromine promoter in the presence of acetic acid, the waste stream will be a slurry that comprises aromatic acids, cobalt and/or manganese salts as acetates, bromides, terephthalates and benzoates, residual amounts of acetic acid, and water.

According to the present invention, the source of metal ions and carbonate or bicarbonate ions to be added into the waste stream to produce a carbonate salt precipitate of the heavy metal can be any salt or mixture of salts that provide soluble carbonate or bicarbonate ions. In some embodiments, the source of carbonate or bicarbonate ions is added until pH is 7 to 9.5 in order to produce carbonate salt precipitate of the heavy metal. In some embodiments, the source of carbonate or bicarbonate ions is added until pH is 8 to 9. In some embodiments, the source of carbonate or bicarbonate ions is added until pH is 8.5.

The method of separating the heavy metal carbonate salt precipitate from the waste stream includes but is not limited to: vacuum filtering, bag type filtering, plate type filtering, cross-flow filtering, centrifugation filtering, Don type, hydracyclone or hyperflux type filtering.

One can also quantitate the sodium ions in the recovered heavy metal carbonate salt precipitate. Means of quantitating the sodium ions are well known in the art. For example, one can quantitate the amount of sodium ions by determining the ratio of sodium ions over the heavy metal ions in the recovered precipitate, for instance, the cobalt/sodium ratio in the recovered precipitate.

When the source of metal ions and carbonate or bicarbonate ions is potassium carbonate, potassium bicarbonate, or a mixture thereof, the alkali solution used to wash the heavy metal carbonate salt precipitate can be potassium hydroxide.

A process according to the present invention can optionally comprise washing the precipitate, which has been washed with alkali solution, with water before the precipitate comprising the heavy metal ions is recovered.

A process according to the present invention can also optionally comprise converting the heavy metal carbonate salt into catalyst suitable for use in the aromatic carboxylic acid process. As described above, cobalt and/or manganese carbonate recovered from a terephthalic acid process catalyzed by cobalt and/or manganese acetate according to the present invention can be converted into cobalt and/or manganese acetate and reused in the terephthalic acid process.

In some embodiments, the washing of the heavy metal carbonate salt precipitate is performed without resuspending the precipitate. As used in this application, the term "resuspending" refers to the act of intentionally putting the settled precipitate back into suspension and holding it in suspension while the washing is being conducted.

It will be recognized by those of ordinary skill in the art of cobalt recovery that the present invention can be applied to many other industrial processes where cobalt ions need to be recovered. According to another aspect of the present invention, a process for recovering cobalt from a liquid medium containing a basic cobalt salt comprises: (a) producing a cobalt carbonate precipitate by adding a source of metal ions and carbonate or bicarbonate ions into the liquid medium; (b) separating the cobalt carbonate precipitate from the liquid medium; (c) washing the cobalt carbonate precipitate with an alkali solution having metal ions therein, wherein the metal ions in the alkali solution are the same as the metal ions in the source of metal ions and carbonate or bicarbonate ions, the washing being performed without resuspending the precipitate; and (d) recovering cobalt from the washed precipitate in the form of cobalt carbonate.

According to the present invention, the source of metal ions and carbonate or bicarbonate ions to be added into the liquid medium can be any salt or mixture of salts that provide soluble carbonate or bicarbonate ions. Examples of suitable source of carbonate or bicarbonate ions include sodium carbonate, sodium bicarbonate, a mixture of sodium carbonate and sodium bicarbonate, potassium carbonate, potassium bicarbonate, and a mixture of potassium carbonate and potassium bicarbonate. In some embodiments, it is sodium carbonate, sodium bicarbonate, or a mixture thereof.

When the source of metal ions and carbonate or bicarbonate ions is sodium carbonate, sodium bicarbonate, or a mixture thereof, the alkali solution used to wash the cobalt carbonate precipitate can be sodium hydroxide. Typically, the concentration of sodium hydroxide solution used is at least 0.5%. Preferably, the concentration is at least 1%. More preferably, sodium hydroxide solution of at least 5% is used.

One may wish to decide the purity of the recovered cobalt. Methods to decide the purity of the recovered cobalt is well known in the art. For example, one may quantitate the purity by determining the cobalt/sodium ratio in the recovered cobalt carbonate. In some embodiments, the cobalt/sodium ratio in the recovered cobalt carbonate is at least 10. In some embodiments, it is at least 15. In some embodiments, it is at least 20.

As used in this application, the term "resuspending" refers to the act of intentionally putting the settled precipitate back into suspension and holding it in suspension while the washing is being conducted.

One can use the process to recover cobalt from a liquid medium containing any soluble basic cobalt salt, such as cobalt acetate and cobalt oxide.

The process optionally comprises converting the recovered cobalt carbonate to the same basic cobalt salt as in the liquid medium from which it is recovered. In one embodiment, basic cobalt salt in the liquid medium is cobalt acetate.

In one embodiment, the source of metal ions and carbonate or bicarbonate ions used to produce the cobalt carbonate precipitate is sodium carbonate, sodium bicarbonate or a mixture thereof.

In one embodiment, the alkali solution used to wash the cobalt carbonate precipitate is sodium hydroxide solution. In one embodiment, the concentration of the sodium hydroxide solution is at least 0.5%. In one embodiment, the cobalt/sodium ratio of the recovered cobalt carbonate is at least 10.

In one embodiment, the process further comprises converting the cobalt carbonate into the same basic cobalt salt as in the liquid medium from which the cobalt is recovered.

FIG. 1 illustrates, in schematic form, one embodiment of operating the process of this invention. A waste stream is produced from a terephthalic acid production process using para-xylene feedstock. Para-xylene is reacted with air in the presence of acetic acid and water as the oxidation solvent, cobalt/manganese acetate as the oxidation catalyst, and one or more bromine compounds such as hydrogen bromide as an oxidation promotor. The waste stream, which comprises aromatic acids, cobalt/manganese acetate, bromides, terephthalates and benzoates, residual amounts of acetic acid, and water, passes through separation apparatus 8 before entering agitated precipitation reactor 20 through pipe 16. Sodium carbonate solution enters agitated precipitation reactor 20 through pipe 12. The concentration of the sodium carbonate solution is about 25 wt %. The amount of sodium carbonate solution is controlled so that the pH in agitated precipitation reactor 20 remains within the range of 7-9.5. In agitated precipitation reactor 20, sodium carbonate is reacted with cobalt/manganese acetate to produce cobalt/manganese carbonate precipitate.

After the precipitation reaction is completed, the reaction slurry exits precipitation reactor 20 through pipe 24 and enters separation apparatus 28, where cobalt/manganese carbonate precipitate is separated from the waste solution which comprises sodium ions, acetate ions, residual amounts of acetic acid, and water. Separation apparatus 28 is typically one or more filters. The waste solution exits through pipe 32, while cobalt/manganese carbonate precipitate remains in separation apparatus 28. Sodium hydroxide solution then enters separation apparatus 28 through pipe 36 to wash the cobalt/manganese carbonate precipitate. The concentration of sodium hydroxide is typically at least 0.5%. Preferably, it is at least 1%. More preferably, it is at least 5%. The temperature in separation apparatus 28 is typically 30-50° C. Typically, sodium hydroxide wash is conducted for 5-20 minutes before the wash solution exits through pipe 32.

Preferably, cobalt/manganese carbonate precipitate remains in separation apparatus 28 after sodium hydroxide wash to be washed at least once with water, which enters through pipe 36 and exits through pipe 32 after the wash is completed. Typically, the wash is conducted for 5-20 minutes.

The cobalt/manganese carbonate precipitate is then directed to reconstitution drum 44 through pipe 40. In reconstitution drum 44, cobalt/manganese carbonate is reacted with acetic acid, which enters through pipe 48, and cobalt/manganese acetate is produced. The cobalt/manganese acetate mixture thus produced can be collected and reused as oxidation catalyst for terephthalic acid production.

While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A process for recovering a heavy metal from a waste stream resulting from a process for producing aromatic carboxylic acid by liquid-phase oxidation of an aromatic feedstock compound in the presence of a heavy metal catalyst, comprising:
    a) producing a carbonate salt precipitate of the heavy metal by adding a source of metal ions and carbonate or bicarbonate ions into the waste stream;
    b) separating the carbonate salt precipitate from the waste stream;
    c) washing the precipitate with an alkali solution having metal ions therein, wherein at least a portion of the metal ions in the alkali solution are the same as at least a portion of metal ions in the source of metal ions and carbonate or bicarbonate ions, wherein washing the carbonate salt precipitate is performed without resuspending the precipitate; and
    d) recovering the washed precipitate wherein the washed precipitate comprises the carbonate salt precipitate of the heavy metal ions.

2. The process of claim 1, wherein the aromatic carboxylic acid comprises terephthalic acid.

3. The process of claim 2, wherein the aromatic feedstock compound comprises para-xylene.

4. The process of claim 1, wherein the source of metal ions and carbonate or bicarbonate ions is added until pH is 7 to 9.5.

5. The process of claim 1, further comprising washing the washed precipitate with water before recovering the precipitate.

6. The process of claim 1, wherein the source of metal ions and carbonate or bicarbonate ions is sodium carbonate, sodium bicarbonate or a mixture thereof.

7. The process of claim 6, wherein the alkali solution in step (c) is sodium hydroxide solution.

8. The process of claim 1, further comprising converting the carbonate salt of the heavy metal into catalyst suitable for use in the process for producing aromatic carboxylic acid.

9. The process of claim 7, wherein the precipitate recovered in step (d) comprises sodium ions, and wherein the process further comprising quantitating the sodium ions in the precipitate recovered in step (d).

10. The process of claim 1, wherein the waste stream comprises acetate ions.

11. The process of claim 1, wherein the waste stream comprises cobalt acetate and manganese acetate.

12. The process of claim 9, wherein the atomic ratio of cobalt to sodium in the precipitate recovered in step (d) is at least 10.

13. A process for recovering cobalt from a liquid medium containing a basic cobalt salt, comprising:
    a) producing a cobalt carbonate precipitate by adding a source of metal ions and carbonate or bicarbonate ions into the liquid medium;
    b) separating the cobalt carbonate precipitate from the liquid medium;
    c) washing the cobalt carbonate precipitate with an alkali solution having metal ions therein, wherein the metal ions in the alkali solution are the same as the metal ions in the source of metal ions and carbonate or bicarbonate ions, the washing being performed without resuspending the precipitate; and
    d) recovering cobalt from the washed precipitate in the form of cobalt carbonate.

14. The process of claim 13, wherein the basic cobalt salt is cobalt acetate.

15. The process of claim 13, wherein the source of metal ions and carbonate or bicarbonate ions is sodium carbonate, sodium bicarbonate or a mixture thereof.

16. The process of claim 15, wherein the alkali solution is sodium hydroxide solution.

17. The process of claim 15, wherein the concentration of the sodium hydroxide solution is at least 0.5%.

18. The process of claim 13, further comprising converting the cobalt carbonate into the basic cobalt salt.

19. The process of claim 16, wherein the washed precipitate of step (c) comprises sodium ions, and the atomic ratio of cobalt to sodium in precipitate of step (c) is at least 10.

20. A process for recovering a heavy metal from a waste stream resulting from a process for producing aromatic carboxylic acid by liquid-phase oxidation of an aromatic feedstock compound in the presence of a heavy metal catalyst, comprising:
    a) producing a carbonate salt precipitate of the heavy metal by adding a source of metal ions and carbonate or bicarbonate ions into the waste stream; then
    b) separating the carbonate salt precipitate from the waste stream; then
    c) washing the separated carbonate salt precipitate with a solution of metal hydroxide, wherein at least a portion of the metal of the metal hydroxide solution is the same as the metal of at least a portion of the metal ions in the source of metal ions and carbonate or bicarbonate ions, the washing being performed without resuspending the precipitate; and then
    d) recovering the washed precipitate wherein the washed precipitate comprises the carbonate salt precipitate of the heavy metal ions.

21. The process of claim 20, wherein the metal of the metal hydroxide solution is sodium and the metal of the metal ions of the source of metal ions and carbonate or bicarbonate ions is sodium.

* * * * *